United States Patent
Wan et al.

(10) Patent No.: US 9,783,546 B2
(45) Date of Patent: Oct. 10, 2017

(54) COMPOUNDS

(71) Applicant: GlaxoSmithKline Intellectual Property Development Limited, Brentford, Middlesex (GB)

(72) Inventors: Zehong Wan, Shanghai (CN); Xiaomin Zhang, Shanghai (CN); Jian Wang, Shanghai (CN)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 0 days.

(21) Appl. No.: 15/327,685

(22) PCT Filed: Jul. 21, 2015

(86) PCT No.: PCT/CN2015/084607
§ 371 (c)(1),
(2) Date: Jan. 20, 2017

(87) PCT Pub. No.: WO2016/011931
PCT Pub. Date: Jan. 28, 2016

(65) Prior Publication Data
US 2017/0204108 A1    Jul. 20, 2017

(30) Foreign Application Priority Data
Jul. 22, 2014  (WO) ................ PCT/CN2014/000695

(51) Int. Cl.
*C07D 487/14*    (2006.01)
*A61K 31/519*    (2006.01)

(52) U.S. Cl.
CPC .................................. *C07D 487/14* (2013.01)

(58) Field of Classification Search
None
See application file for complete search history.

(56) References Cited

U.S. PATENT DOCUMENTS

2014/0080055 A1    3/2014  Hatakeyama et al.

FOREIGN PATENT DOCUMENTS

| CN | WO 2012080497 A2 * | 6/2012 | ............ A61K 31/00 |
|---|---|---|---|
| CN | 103927116 A | 5/2014 | |
| CN | 103842362 A | 6/2014 | |
| WO | WO 03/041712 A1 | 5/2003 | |
| WO | WO 2009/147476 A1 | 12/2009 | |
| WO | WO 2012/037782 A1 | 3/2012 | |
| WO | WO 2013/014185 A1 | 1/2013 | |
| WO | WO 2013/059278 A2 | 4/2013 | |
| WO | WO 2014/114249 A1 | 7/2014 | |
| WO | WO 2014/114694 A1 | 7/2014 | |

* cited by examiner

*Primary Examiner* — Michael Barker
(74) *Attorney, Agent, or Firm* — Feng Xu; William R. Majarian

(57) ABSTRACT

The present invention relates to novel compounds that inhibit $Lp-PLA_2$ activity, processes for their preparation, to compositions containing them and to their use in the treatment of diseases associated with the activity of $Lp-PLA_2$, for example atherosclerosis, Alzheimer's disease.

16 Claims, No Drawings

COMPOUNDS

RELATED APPLICATION

This application is a 371 of International Application No. PCT/CN2015/084607, filed 21 Jul. 2015, which claims benefit of PCT Application PCT/CN2014/000695 filed 22 Jul. 2014.

FIELD OF THE INVENTION

The present invention relates to novel tricyclic imidazopyrimidinone compounds, processes for their preparation, intermediates useful in their preparation, pharmaceutical compositions containing them, and their use in therapy for the treatment of diseases mediated by Lp-PLA$_2$.

BACKGROUND OF THE INVENTION

Lipoprotein-associated phospholipase A$_2$ (Lp-PLA$_2$) previously known as platelet-activating factor acetylhydrolase (PAF-AH), is a phospholipase A2 enzyme involved in hydrolysis of lipoprotein lipids or phospholipids. Lp-PLA$_2$ travels with low-density lipoprotein (LDL) and rapidly cleaves oxidized phosphatidylcholine molecules derived from the oxidation of LDL. (See e.g., Zalewski A, et al., Arterioscler. Thromb. Vasc. Biol., 25, 5, 923-31(2005)). Lp-PLA$_2$ hydrolyzes the sn-2 ester of the oxidized phosphatidylcholines to give lipid mediators, lyso-phosphatidylcholine (lysoPC) and oxidized nonesterified fatty acids (NEFAs). It has been observed that lysoPC and NEFAs elicit inflammatory responses. (See e.g., Zalewski A, et al. (2005)).

A number of Lp-PLA$_2$ inhibitors and/or uses thereof have been previously described. (See. for example, published patent application nos. WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, and WO08/048866.) Disclosed uses include treating disease that involves or is associated with endothelial dysfunction, disease that involves lipid oxidation in conjunction with Lp-PLA$_2$ activity (e.g., associated with the formation of lysophosphatidylcholine and oxidized free fatty acids), and disease that involves activated monocytes, macrophages or lymphocytes or which is associated with increased involvement of monocytes, macrophages or lymphocytes. Examples of diseases include atherosclerosis (e.g. peripheral vascular atherosclerosis and cerebrovascular atherosclerosis), diabetes, hypertension, angina pectoris, after ischaemia and reperfusion, rheumatoid arthritis, stroke, inflammatory conditions of the brain such as Alzheimer's disease, various neuropsychiatric disease such as schizophrenia, myocardial infarction, ischaemia, reperfusion injury, sepsis, acute and chronic inflammation, and psoriasis.

Lp-PLA$_2$ inhibitors and/or uses thereof are also reported, for example, in PCT Publication Nos. WO05/003118 (and its Canadian family member CA 2530816A1); WO06/063811; WO06/063813 and WO 2008/141176; JP 200188847; and US Published Patent Application Nos. US 2008/0279846 Al, US 2010/0239565 A1, and US 2008/0280829 A1.

Other researchers have studied the effects related to Lp-PLA$_2$ and inhibitors thereof. For example, research data has also indicated that LysoPC promotes atherosclerotic plaque development, which can ultimately lead to the formation of a necrotic core. (See e.g., Wilensky et al., Current Opinion in Lipidology, 20, 415-420 (2009)). In addition, the effect of Lp-PLA$_2$ inhibitors on atherosclerotic plaque composition was demonstrated in a diabetic and hypercholesterolemic porcine model of accelerated coronary atherosclerosis. (See e.g., Wilensky et al., Nature Medicine, 10, 1015-1016 (2008)). These research results provided further evidence that Lp-PLA$_2$ inhibitors may be used to treat atherosclerosis.

Additional studies indicate that high Lp-PLA$_2$ activity is associated with high risk of dementia, including Alzheimer's disease (AD) (See e.g., Van Oijen, et al. Annals of Neurology, 59,139 (2006)). Higher levels of oxidized LDL have also been observed in AD patients (See e.g., Kassner et al. Current Alzheimer Research, 5, 358-366 (2008); Dildar, et al., Alzheimer Dis Assoc Disord, 24, April-June (2010); Sinem, et al. Current Alzheimer Research, 7, 463-469 (2010)). Further, studies show that neuroinflammation is present in AD patients and multiple cytotoxic inflammatory cytokines are up-regulated in AD patients. (See e.g., Colangelo, et al., Journal of Neuroscience Research, 70, 462-473 (2002); Wyss-Coray, Nature Medicine, 12, Sept. (2006)). Research has shown that LysoPC function is a pro-inflammatory factor inducing multiple cytotoxic inflammatory cytokine release (See Shi, et al. Atherosclerosis, 191, 54-62 (2007)). Therefore, these studies provide additional evidence that that the inhibitors of Lp-PLA$_2$ can be used to treat AD by inhibiting activity of Lp-PLA$_2$ and reducing lysoPC production.

In addition, use of an Lp-PLA$_2$ inhibitor in a diabetic and hypercholesterolemia swine model demonstrated that blood-brain-barrier leakage and brain amyloid beta protein (Aβ) burden, the pathological hallmarks of Alzheimer's disease, were reduced. (See U.S. Patent Application Publication No. 2008/0279846). This publication describes several uses of Lp-PLA$_2$ inhibitors for treating diseases associated with blood-brain-barrier leakage, including, e.g., Alzheimer's disease and vascular dementia.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See e.g., Perry, Acta Neuropathol, 120, 277-286 (2010)). As discussed above, Lp-PLA$_2$ inhibitors can reduce inflammation, for example, reducing multiple cytokine release by suppressing lysoPC production. (See e.g., Shi, et al. Atherosclerosis 191, 54-62 (2007)). Thus, inhibiting Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (See, e.g., Wilensky et al., Current Opinion in Lipidology, 20, 415-420 (2009)). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-PLA$_2$ and the association between localized inflammatory processes and diabetic retinopathy, it is postulated that Lp-PLA$_2$ can be used to treat diabetic ocular disease.

Glaucoma and age-related macular degeneration (AMD) are retina neurodegenerative diseases. Studies suggest that inflammation, including TNF-alpha signaling, may play an important role in the pathogenesis of glaucoma and AMD (See e.g., Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See e.g., Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$, attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention relates to compounds having a structure of

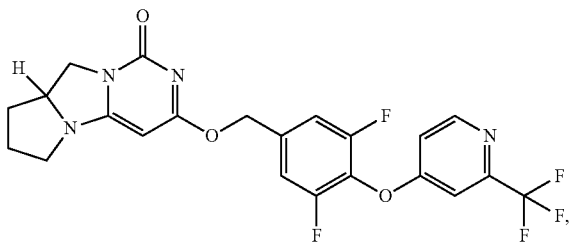

and salts thereof (e.g., pharmaceutically acceptable salts thereof).

In a further aspect, the invention relates to compounds having a structure of

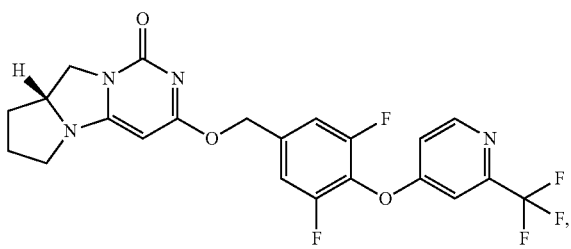 [SMILES: O=c1nc(OCc2cc(F)c(Oc3ccnc(C(F)(F)F)c3)c(F)c2)cc2n1C[C@H]1CCCN21]

and salts thereof (e.g., pharmaceutically acceptable salts thereof).

In another aspect, the invention relates to compounds having a structure of

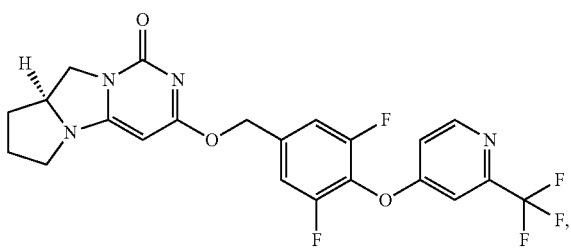 [SMILES: O=c1nc(OCc2cc(F)c(Oc3ccnc(C(F)(F)F)c3)c(F)c2)cc2n1C[C@@H]1CCCN21]

and salts thereof (e.g. pharmaceutically acceptable salt thereof).

This invention also relates to a pharmaceutical composition comprising compounds described in this invention and a pharmaceutically acceptable excipient.

The invention also relates to methods of treating or preventing a disease associated with the activity of Lp-PLA$_2$, which comprises administering to a subject in need thereof with a therapeutically effective amount of a compound of the invention described herein. The disease may be associated with the increased involvement of monocytes, macrophages or lymphocytes; with the formation of lyso-phosphatidylcholine and oxidized free fatty acids; with lipid oxidation in conjunction with Lp-PLA$_2$ activity; or with endothelial dysfunction.

This invention also provides methods of treating or preventing a disease by inhibiting Lp-PLA$_2$ activity. Exemplary diseases include, but are not limited to, neurodegeneration disease (e.g., Alzheimer's disease, Parkinson's disease, Huntington's disease, vascular dementia), atherosclerosis, stroke, metabolic bone disorder (e.g., bone marrow abnormalities), dyslipidemia, Paget's diseases, type II diabetes, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD), psoriasis, and multiple sclerosis. The methods comprise administering a therapeutically effective amount of a compound of this invention to a subject in need thereof. It is not intended that the present invention is limited to any particular stage of the disease (e.g. early or advanced).

This invention also provides methods of treating or preventing Alzheimer's disease. The methods comprise administering to a subject in need thereof a therapeutically effective amount of a compound of this invention.

This invention also provides methods of treating or preventing atherosclerosis. The methods comprise administering to a subject in need thereof a therapeutically effective amount of a compound of this invention.

This invention also provides methods of decreasing beta amyloid (also referred to as "Aβ") accumulation in the brain of a subject. The methods comprise administering to a subject in need thereof a therapeutically effective amount of a compound of the present invention. In certain embodiment, the beta amyloid is Abeta-42.

This invention also provides methods for treating or preventing ocular diseases by administering a compound of this invention. In certain embodiment, this invention provides methods of treating macular edema, which comprises administering to the subject a therapeutically effective amount of a compound of this invention. In certain embodiment, the macular edema is associated with diabetic ocular disease, for example, diabetic macular edema or diabetic retinopathy. In one embodiment, the macular edema is associated with posterior uveitis.

This invention also provides a use of compounds of this invention in the manufacture of a medicament for treating or preventing diseases described herein.

This invention also provides compounds of this invention for use in the treatment or prevention described herein.

DETAILED DESCRIPTION OF THE INVENTION

As used in the description of the embodiments of the invention and the appended claims, the singular forms "a", "an" and "the" are intended to include the plural forms as well, unless the context clearly indicates otherwise. Also, as used herein, "and/or" refers to encompasses any and all possible combinations of one or more of the associated listed items. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

A. Definitions

As used herein, unless otherwise indicated, "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

As used herein, unless otherwise indicated, "neurodegeneration disease" as used herein refers to a varied assortment of central nervous system disorder characterized by gradual and progressive loss of neural tissue and/or neural tissue function. A neurodegeneration disease is a class of neurological disease where the neurological disease is characterized by a gradual and progressive loss of neural tissue, and/or altered neurological function, typically reduced neurological function as a result of a gradual and progressive loss of neural tissue. In certain embodiments, the neurodegeneration diseases described herein include neurodegeneration diseases where there is a defective blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

As used herein, unless otherwise indicated, "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyrus), vascular dementia due to hemorrhagic lesions, small vessel disease (including, e.g. vascular dementia due to lacunar lesions and Binswanger disease), and mixed dementia.

As used herein, unless otherwise indicated, "blood-brain barrier" or "BBB" are used interchangeably herein, and are used to refer to the permeable barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

As used herein, unless otherwise indicated, "metabolic bone disease" as used herein refers to a varied assortment of bone diseases characterized by gradual and progressive loss of bone tissue. Metabolic bone diseases described herein are metabolic bone diseases where there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

As used herein, unless otherwise indicated, "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteoid synthesis.

As used herein, unless otherwise indicated, "osteoporosis" refers to conditions in which mineral and/or bone matrix are decreased and/or bone mass is reduced.

As used herein, unless otherwise indicated, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease. In one embodiment, "treat" "treating" or "treatment" in reference to Alzheimer's disease means: to slow the progression of congnitive function decline.

As used herein, unless otherwise indicated, "prevent", "preventing" or "prevention" means the prophylactic administration of a drug to diminish the likelihood of the onset of or to delay the onset of a disease or biological manifestation thereof.

As used herein, unless otherwise indicated, "subject" means a mammalian subject (e.g., dog, cat, horse, cow, sheep, goat, monkey, etc.), and particularly human subjects including both male and female subjects, and including neonatal, infant, juvenile, adolescent, adult and geriatric subjects, and further including various races and ethnicities including, but not limited to, white, black, Asian, American Indian and Hispanic.

As used herein, unless otherwise indicated, "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, unless otherwise indicated, the term "therapeutically effective amount" means any amount which, as compared to a corresponding subject who has not received such amount, results in treating or preventing a disease, but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

B. Compounds

One aspect of the present invention provides compounds having the structure of 3-((3, 5-difluoro-4-((2-(trifluoromethyl)pyridin-4-yl)oxy)benzyl)oxy)-7, 8, 8a, 9-tetrahydropyrrolo[1',2':3,4]imidazo[1,2-c]pyrimidin-1(6H)-one

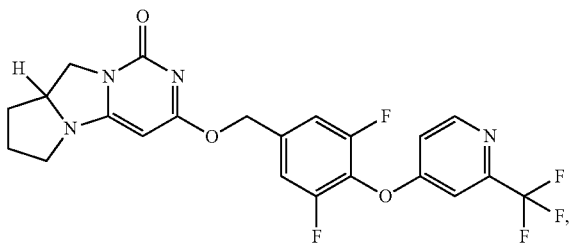 [SMILES: O=c1nc(OCc2cc(F)c(Oc3ccnc(C(F)(F)F)c3)c(F)c2)cc2n1CC1CCCN21]

and salts thereof.

Another aspect of the present invention provides compounds having the structure of 3-((3, 5-difluoro-4-((2-(trifluoromethyl)pyridin-4-yl)oxy)benzyl)oxy)-7, 8, 8a, 9-tetrahydropyrrolo[1',2': 3,4]imidazo[1,2-c]pyrimidin-1(6H)-one

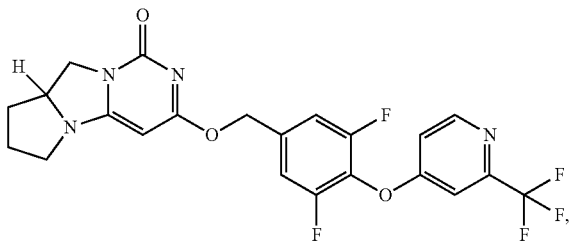 [SMILES: O=c1nc(OCc2cc(F)c(Oc3ccnc(C(F)(F)F)c3)c(F)c2)cc2n1CC1CCCN21]

and pharmaceutically acceptable salts thereof.

In one embodiment, this invention relates to compounds having the structure of (R)-3-((3, 5-difluoro-4-((2-(trifluoromethyl) pyridin-4-yl) oxy) benzyl) oxy)-7, 8, 8a, 9-tetra hydropyrrolo[1',2': 3,4]imidazo[1,2-c]pyrimidin-1(6H)-one

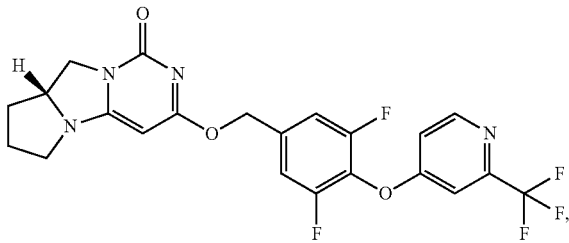 [SMILES: O=c1nc(OCc2cc(F)c(Oc3ccnc(C(F)(F)F)c3)c(F)c2)cc2n1C[C@H]1CCCN21]

and salts thereof.

In one embodiment, this invention relates to compounds having the structure of (R)-3-((3, 5-difluoro-4-((2-(trifluoromethyl) pyridin-4-yl) oxy) benzyl) oxy)-7, 8, 8a, 9-tetra hydropyrrolo[1',2': 3,4]imidazo[1,2-c]pyrimidin-1(6H)-one

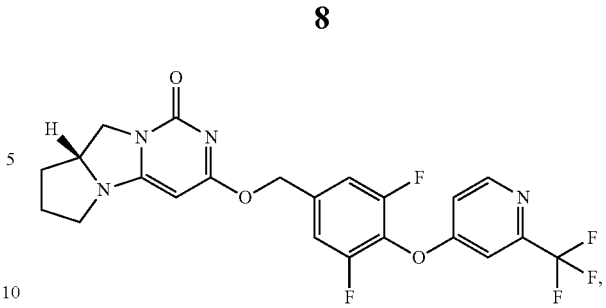

and pharmaceutically acceptable salts thereof.

In another embodiment, the invention relates to a compound having the structure of (R)-3-((3, 5-difluoro-4-((2-(trifluoromethyl) pyridin-4-yl) oxy) benzyl) oxy)-7, 8, 8a, 9-tetra hydropyrrolo[1',2': 3,4]imidazo[1,2-c]pyrimidin-1(6H)-one

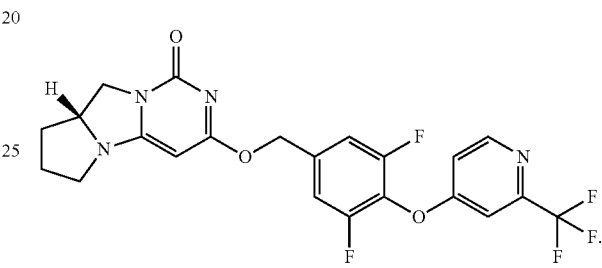

In one embodiment, the invention relates to a compound having the structure of a pharmaceutically acceptable salt of (R)-3-((3, 5-difluoro-4-((2-(trifluoromethyl) pyridin-4-yl) oxy) benzyl) oxy)-7, 8, 8a, 9-tetra hydropyrrolo[1',2':3,4] imidazo[1,2-c]pyrimidin-1(6H)-one

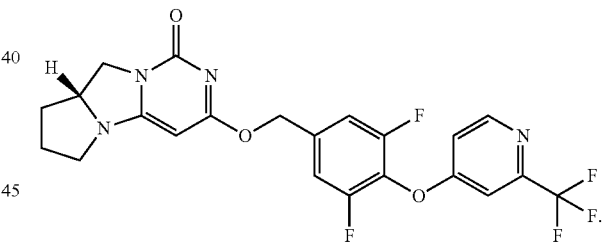

In another embodiment, the invention relates to a compound having the structure of (S)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

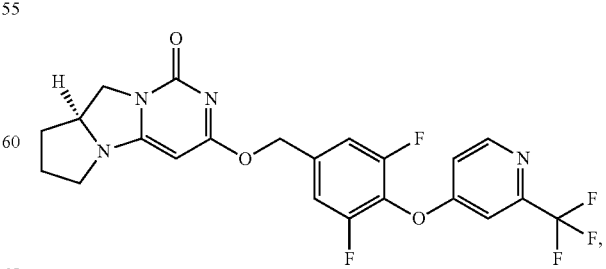

and salts thereof.

In another embodiment, the invention relates to a compound having the structure of (S)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

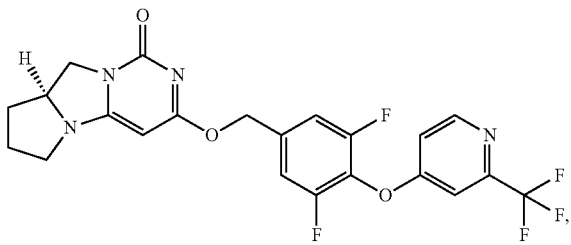 [SMILES: O=c1nc(OCc2cc(F)c(Oc3ccnc(C(F)(F)F)c3)c(F)c2)cc2n1C[C@@H]1CCCN21]

and pharmaceutically acceptable salts thereof.

In one embodiment, the invention is related to a compound having the structure of (S)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

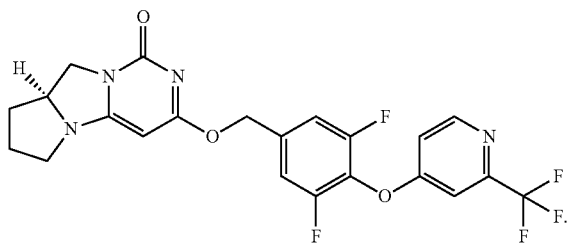

In one embodiment, the invention is related to a compound having the structure of a pharmaceutically acceptable salt of (S)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

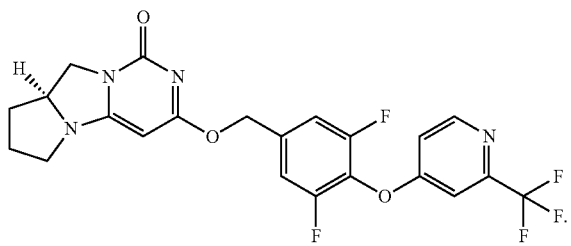

The compounds described above, salts (e.g., pharmaceutically acceptable salts) thereof may exist in stereoisomeric forms (e.g., it contains one or more asymmetric carbon atoms). The individual stereoisomers (enantiomers and diastereomers) and mixtures of these are included within the scope of the present invention. The scope of the present invention includes purified enantiomers or enantiomerically/diastereomerically enriched mixtures. The different isomeric forms may be separated or resolved one from the other by conventional methods (e.g. chiral HPLC), or any given isomer may be obtained by conventional synthetic methods e.g. stereospecific or asymmetric syntheses.

The invention also includes various deuterated forms of compounds described above, and salts (e.g., pharmaceutically acceptable salts) thereof. Each available hydrogen atom attached to a carbon atom may be independently replaced with a deuterium atom. A person of ordinary skill in the art will know how to synthesize deuterated forms of compounds described above, and salts (e.g., pharmaceutically acceptable salts) thereof. Commercially available deuterated starting materials may be employed in the preparation of deuterated forms of compounds described above, and salts (e.g., pharmaceutically acceptable salts) thereof, or they may be synthesized using conventional techniques employing deuterated reagents (e.g. lithium aluminum deuteride).

In addition to the free base of the compounds described herein, the salt form of the compounds is also within the scope of the present invention. The salts or pharmaceutically acceptable salts of the compounds described herein may be prepared in situ during the final isolation and purification of the compound, or by separately reacting the purified compound in its free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain a basic group and are therefore capable of forming pharmaceutically acceptable acid addition salts by treatment with a suitable acid. Suitable acids include pharmaceutically acceptable inorganic acids and pharmaceutically acceptable organic acids. These salts may be crystalline or amophorus. Exemplary pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

The compounds described herein, their salts (e.g., pharmaceutically acceptable salts), deuterated forms, solvates or hydrates thereof, may exist in one or more polymorphic form. Therefore, in a further aspect, the invention provides a polymorph of a compound defined herein, their salts (e.g., pharmaceutically acceptable salts), or a polymorph of a solvate or hydrate of a compound described herein or a salt (e.g., pharmaceutically acceptable salt) thereof.

The compounds described above and salts (including pharmaceutically acceptable salts) thereof may be in the form of a solvate. For solvates of the compounds described above, including solvates of salts of the compounds described above, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethylsulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Solvates include stoichiometric solvates as well as compositions containing variable amounts of the incorporated solvent(s), e.g. a hydrate includes stoichiometic hydrates and compositions containing variable amounts of water.

The invention also includes isotopically labeled compounds and salts, which are identical to compounds described above or salts thereof, but for the fact that one or more atoms are replaced by an atom having an atomic mass or mass number different from the atomic mass or mass number most commonly found in nature. Examples of isotopes that can be incorporated into compounds described above or salts thereof isotopes of hydrogen, carbon, nitrogen, fluorine, such as $^3$H, $^{11}$C, $^{14}$C and $^{18}$F. Such isotopically labeled compound described above or salts thereof are useful in drug and/or substrate tissue distribution assays. For example, $^{11}$C and $^{18}$F isotopes are useful in PET (positron emission tomography). PET is useful in brain imaging. Isotopically-labeled compounds described above and salts thereof can generally be prepared by carrying out the procedures disclosed below, by substituting a readily available isotopically-labeled reagent for a non-isotopically labeled reagent. In one embodiment, compounds described above or salts thereof are not isotopically labeled.

As used herein, the terms "compound(s) of the invention" or "compound(s) of the present invention" mean a compound described above, as defined herein, in any form, i.e., any salt or non-salt form (e.g., as a free base form, or as a salt, for example, a pharmaceutically acceptable salt thereof), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms. In the context of pharmaceutical composition and methods of treatment discussed herein, the terms of "compounds of the invention" mean a compound described above, in the form of any pharmaceutically acceptable salt thereof or non-salt form (e.g., as a free base form), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, a compound of the invention includes a compound described above, or a salt thereof, for example a pharmaceutically acceptable salt thereof. Representative compounds of this invention include the specific compounds described.

All temperatures are reported in degrees Celsius. All other abbreviations are as described in the ACS Style Guide (American Chemical Society, Washington, D.C., 1986) unless the abbreviations are specifically defined below.

LCMS Conditions:
1) Acidic conditions:
Mobile phase: water containing 0.05% TFA/0.05% acetonitrile
Column: Agilent SB-C18 4.6×30 mm-1.8 microns
Detection: MS and photodiode array detector (PDA)

2) Basic conditions:
Mobile phase: water containing 10 mmol NH$_4$HCO$_3$/acetonitrile
Column: XBridge™ C18 4.6×50 mm-3.5 microns
Detection: MS and photodiode array detector (PDA)

The chemical name of compuonds described in the present application follows the principle of IUPAC nomenclature.

Abbreviations and Resource Sources
The following abbreviations and resources are used herein below:
ISCO system—Teledyne ISCO (http://www.isco.com/html/seFlashChromatography.html)
r.t/rt/RT—room temperature
ACN—acetonitrile
Aq.—aqueous
CV—column volumes
DCM—dichloromethane
DMF—N,N-dimethylformamide
DMP—Dess-Martin periodinane
DMSO—dimethyl sulfoxide
EtOH—ethanol
EN EtOAc—ethyl acetate
FC—flash chromatography (usually conducted on silica gel column)
sat.—saturated
TEA or Et$_3$N—triethylamine
THF—tetrahydrofuran
PE—petroleum ether

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

In general, the compounds of the present invention may be prepared by standard techniques known in the art and by known processes analogous thereto. General methods for preparing compounds of the present invention are set forth below. All starting material and reagents described in the below general experimental schemes are commercially available.

In the procedures that follow, after each starting material, reference to an intermediate is typically provided. This is provided merely for assistance to the skilled chemist. The starting material may not necessarily have been prepared from the batch referred to.

D1

(1-(2,6-Dichloropyrimidin-4-yl)pyrrolidin-2-yl)methanol

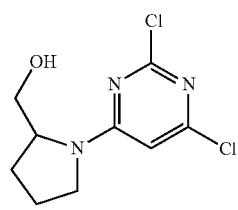 [SMILES: OCC1CCCN1c1cc(Cl)nc(Cl)n1]

To the solution of 2, 4, 6-trichloropyrimidine (2.176 g, 11.86 mmol) and triethylamine (2.76 mL, 19.77 mmol) in acetonitrile (25 mL) was added dropwise pyrrolidin-2-yl-methanol (1.0 g, 9.89 mmol) in acetonitrile (5 mL) at 0° C. The mixture was stirred for 2 hrs at room temperature and collected the solution by filtration, concentrated in vacuum and the residue was purified via silica flash column. After removing solvent, a pale solid of (1-(2, 6-dichloropyrimidin-4-yl) pyrrolidin-2-yl) methanol (1.4 g, 5.64 mmol, 57.1% yield) was afforded.

LC-MS (ESI): m/z 248 [M +H]$^+$; 2.42 min (ret time).
D2

3-Chloro-7,8,8a,9-tetrahydropyrrolo[1',2':3,4]imidazo[1,2-c]pyrimidin-1(6H)-one

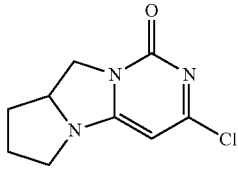 [SMILES: O=c1nc(Cl)cc2n1CC1CCCN21]

To the solution of (1-(2,6-dichloropyrimidin-4-yl)pyrrolidin-2-yl)methanol (300 mg, 1.209 mmol) and triethylamine (0.506 mL, 3.63 mmol) in tetrahydrofuran (15 mL) was added dropwise methanesulfonyl chloride (0.141 mL, 1.814 mmol) in tetrahydrofuran (5 mL) at 0° C. and the mixture was stirred further 10 min at 0° C. The result mixture was concentrated in vacuum and the residue was added acetonitrile (20.00 mL) and potassium carbonate (836 mg, 6.05 mmol). The suspension was refluxed for 4 hrs and filtrated in vacuum, the filtrate was concentrated in vacuum afforded crude product of 3-chloro-7,8,8a,9-tetrahydropyrrolo[1',2':3,4]imidazo[1,2-c]pyrimidin-1(6H)-one (256 mg, 1.209 mmol, 100% yield).
D3

(R)-(1-(2, 6-dichloropyrimidin-4-yl) pyrrolidin-2-yl) methanol

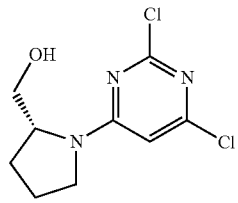 [SMILES: OC[C@H]1CCCN1c1cc(Cl)nc(Cl)n1]

The title compound was prepared by a procedure similar to that described for (1-(2,6-dichloropyrimidin-4-yl)pyrrolidin-2-yl)methanol starting from D-prolinol and 2, 4, 6-trichloropyrimidine.

An exemplary synthesis is provided: To the solution of 2, 4, 6-trichloropyrimidine (3.26 g, 17.80 mmol) and triethylamine (4.13 mL, 29.7 mmol) in acetonitrile (25 mL) was added dropwise D-prolinol (1.456 mL, 14.83 mmol) in acetonitrile (5 mL) at 0° C. The mixture was stirred for 2 hours at room temperature and collected the solution by filtration, concentrated in vacuum and the residue was purified via silica flash column. After removing solvent, a pale solid of (R)-(1-(2, 6-dichloropyrimidin-4-yl) pyrrolidin-2-yl) methanol (2.5 g, 10.08 mmol, 67.9% yield) was afforded.

LC-MS (ESI): m/z 248 [M+H]$^+$; 2.43 min (ret time).
D4

(R)-3-chloro-7,8,8a,9-tetrahydropyrrolo[1',2':3,4]imidazo[1,2-c]pyrimidin-1(6H)-one

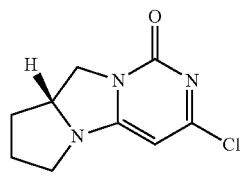 [SMILES: O=c1nc(Cl)cc2n1C[C@H]1CCCN21]

The title compound was prepared by a procedure similar to that described for 3-chloro-7,8,8a,9-tetrahydropyrrolo[1',2':3,4]imidazo[1,2-c]pyrimidin-1(6H)-one starting from (R)-(1-(2, 6-dichloropyrimidin-4-yl) pyrrolidin-2-yl) methanol.

An exemplary synthesis is provided below: To the solution of (R)-(1-(2, 6-dichloropyrimidin-4-yl) pyrrolidin-2-yl) methanol (1.95 g, 7.86 mmol) and triethylamine (3.29 mL, 23.58 mmol) in tetrahydrofuran (15 mL) was added dropwise methanesulfonyl chloride (0.919 mL, 11.79 mmol) in tetrahydrofuran (5 mL) at 0° C. and the mixture was stirred for 10 min at 0° C. The result mixture was concentrated in vacuum and acetonitrile (20.00 mL) and potassium carbonate (3.26 g, 23.58 mmol) was added to the residue. The suspension was refluxed for 4 h and filtrated in vacuum. The filtrate was concentrated in vacuum to afford the title compound (1.663 mg, 7.86 mmol, 100% yield).

LC-MS (ESI): m/z 212 [M+H]$^+$; 1.33 min (ret time).
D5

(S)-(1-(2, 6-dichloropyrimidin-4-yl) pyrrolidin-2-yl) methanol

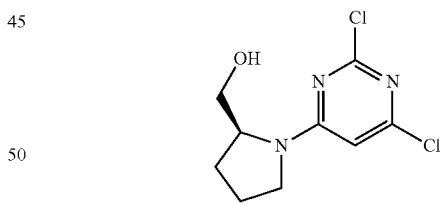

The title compound was prepared by a procedure similar to that described for (1-(2,6-dichloropyrimidin-4-yl)pyrrolidin-2-yl)methanol starting from L-prolinol and 2, 4, 6-trichloropyrimidine.

An exemplary process is provided: To the solution of 2, 4, 6-trichloropyrimidine (3.26 g, 17.80 mmol) and triethylamine (4.13 mL, 29.7 mmol) in acetonitrile (25 mL) was added dropwise L-prolinol (1.456 mL, 14.83 mmol) in acetonitrile (5 mL) at 0° C. The mixture was stirred for 2 hrs at room temperature and collected the solution by filtration, concentrated in vacumn and the residue was purified via silica flash column. The title compound was afforded (2.5 g, 10.08 mmol, 67.9% yield) as a pale solid.

LC-MS (ESI): m/z 248 [M+H]$^+$; 2.43 min (ret time).

D6

(S)-3-chloro-7,8,8a,9-tetrahydropyrrolo[1',2':3,4]imidazo[1,2-c]pyrimidin-1(6H)-one

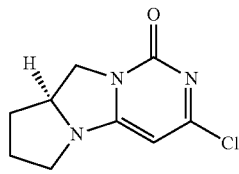 [SMILES: O=c1nc(Cl)cc2n1C[C@@H]1CCCN21]

The title compound was prepared by a procedure similar to that described for 3-chloro-7,8,8a,9-tetrahydropyrrolo[1',2': 3,4]imidazo[1,2-c]pyrimidin-1(6H)-one starting from (S)-(1-(2, 6-dichloropyrimidin-4-yl) pyrrolidin-2-yl) methanol.

An exemplary process is provided: To the solution of (S)-(1-(2, 6-dichloropyrimidin-4-yl) pyrrolidin-2-yl) methanol (400 mg, 1.612 mmol) and triethylamine (0.674 mL, 4.84 mmol) in tetrahydrofuran (15 mL) was added dropwise methanesulfonyl chloride (0.188 mL, 2.418 mmol) in tetrahydrofuran (5 mL) at 0° C. and the mixture was stirred for 10 min at 0° C. The resulting mixture was concentrated in vacuum and the residue was added acetonitrile (20.00 mL) and potassium carbonate (668 mg, 4.84 mmol). The suspension was refluxed for 4 h and filtrated in vacumn. The filtrate was concentrated in vacumn to afford the title compound (341 mg, 1.612 mmol, 100% yield), which was used in the next step directly.

D7

3, 5-Difluoro-4-((2-(trifluoromethyl)pyridin-4-yl)oxy)benzaldehyde

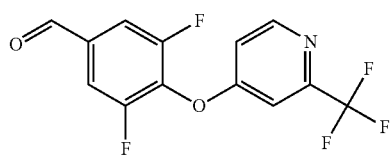 [SMILES: O=Cc1cc(F)c(Oc2ccnc(C(F)(F)F)c2)c(F)c1]

To a solution of 2-(trifluoromethyl)pyridin-4-ol (1.019 g, 6.25 mmol) and K$_2$CO$_3$ (1.727 g, 12.49 mmol) in acetonitrile (250 mL) stirred under nitrogen at 20° C. was added a solution of 3,4,5-trifluorobenzaldehyde (1 g, 6.25 mmol) in acetonitrile (50 mL) dropwise during 5 min. The reaction mixture was stirred at 70° C. for 18 hrs. The reaction mixture was diluted with ethyl acetate (20 mL) and the organic phase was washed with water (2×20 mL), saturated brine (20 mL), dried over sodium sulphate and evaporated in vacuo to give the title compound (2.0 g, 6.02 mmol, 96% yield) as a brown gum.

LC-MS (ESI): m/z 304 [M+H]$^+$; 3.64 min (ret time).

An exemplary process is provided: To a solution of 3,4,5-trifluorobenzaldehyde (2356 mg, 14.72 mmol) and 2-(trifluoromethyl)pyridin-4-ol (2000 mg, 12.26 mmol) in N,N-dimethylformamide (6 mL), K$_2$CO$_3$ (3390 mg, 24.53 mmol) was added. The mixture was irradiated with a microwave at 110° C. and stirred for 3 h, and concentrated. The crude product was washed with EtOAc, and then filtered. The organic phase was concentrated to afford the title compound (4000 mg, 13.19 mmol, 55.9% yield) as a oil.

LC-MS (ESI): m/z 304 [M+H]$^+$; 1.06 min (ret time).

D8

(3,5-Difluoro-4-((2-(trifluoromethyl)pyridin-4-yl)oxy)phenyl)methanol

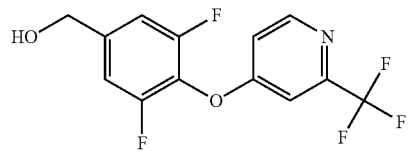 [SMILES: OCc1cc(F)c(Oc2ccnc(C(F)(F)F)c2)c(F)c1]

To a solution of 3,5-difluoro-4-((2-(trifluoromethyl)pyridin-4-yl)oxy)benzaldehyde (50 g, 165 mmol) in methanol (400 mL) was added NaBH$_4$ (3.12 g, 82 mmol) at 0° C. for 10 min. The reaction progress was monitored by TLC and mobile phase was 30% EtOAc in PE. The reaction mixture was quenched with ice water (200 mL) and evaporated under reduced pressure to remove methanol and crude was diluted with ethyl acetate (200 mL) and water (200 mL), organic layer was separated and washed with brine solution (100 mL), dried over Na$_2$SO$_4$ evaporated completely and afforded crude product 50 g, washed with PE and dried to afford the title compound (45 g, 144 mmol, 88% yield) as a white solid.

LC-MS (ESI): m/z 306 [M+H]$^+$: 2.13 min (ret time).

An exemplary process is provided: To a solution of 3,5-difluoro-4-((2-(trifluoromethyl)pyridin-4-yl)oxy)benzaldehyde (4 g, 13.19 mmol) in methanol (30 mL) was added NaBH$_4$ (0.25 g, 6.60 mmol) at 0° C. for 10 min in portion. The reaction mixture was stirred at 5° C. for 0.5 h, concentrated, and dissolved in water, then extracted with EtOAc. The combined organic phase was washed with brine, dried over anhydrous Na$_2$SO$_4$, filtered, and concentrated. The crude product was purified by silica gel column (PE/EtOAc 5:1 to 1:1) to afford the title compound (3.9 g, 12.61 mmol, 96% yield) as a white solid.

LC-MS (ESI): m/z 306 [M+H]$^+$; 1.65 min (ret time).

D9

3-((3, 5-Difluoro-4-((1-methyl-1H-pyrazol-4-yl)oxy)benzyl)oxy)-7,8, 8a, 9-tetrahydro pyrrolo [1', 2':3, 4] imidazo [1, 2-c] pyrimidin-1(6H)-one

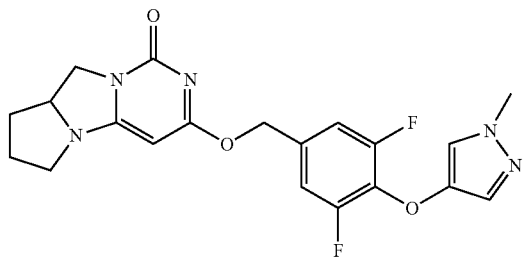 [SMILES: Cn1cc(Oc2c(F)cc(COc3cc4n(c(=O)n3)CC3CCCN43)cc2F)cn1]

To the solution of 3-chloro-7,8,8a,9-tetrahydropyrrolo[1',2':3,4]imidazo[1,2-c]pyrimidin-1(6H)-one (85 mg, 0.402 mmol) and (3,5-difluoro-4-((1-methyl-1H-pyrazol-4-yl)oxy)phenyl)methanol (96 mg, 0.402 mmol) in N,N-dimethylformamide (10 mL), sodium hydride (48.2 mg, 1.205 mmol) was added at 0° C. and stirred further 10 min. The result mixture was quenched and purified via C-18 flash column, removed the solvent to afford white solid of 3-((3, 5-difluoro-4-((1-methyl-1 H-pyrazol-4-yl)oxy)benzyhoxy)-7,8,8a,9-tetrahydropyrrolo[1',2':3,4]imidazo[1,2-c]pyrimidin-1 (6H)-one (55 mg, 0.126 mmol, 31.3 yield).

LC-MS (ESI): m/z 416 [M+H]$^+$; 3.55 min (ret time).

$^1$H NMR (400 MHz, DMSO-d$_6$): δ 7.61 (s, 1H), 7.32-7.27 (m, 3H), 5.34 (s, 1H), 5.30-5.23 (q, 2H), 4.10-4.01 (m, 2H), 3.89-3.85 (m, 1H), 3.73 (s, 3H), 3.40-3.28 (m, 2H), 2.03-1.87 (m, 3H), 1.49-1.42 (m, 1H).

Examples

E1

(R)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

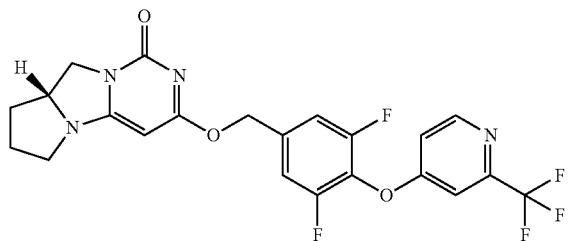 [SMILES: O=c1nc(OCc2cc(F)c(Oc3ccnc(C(F)(F)F)c3)c(F)c2)cc2n1C[C@H]1CCCN21]

To a solution of (R)-3-chloro-7,8,8a,9-tetrahydropyrrolo[1',2':3,4]imidazo[1,2-c]pyrimidin-1(6H)-one (85 mg, 0.402 mmol) and (3,5-difluoro-4-((2-(trifluoromethyl)pyridin-4-yl)oxy)phenyl)methanol (123 mg, 0.402 mmol) in DMF (10 mL) was added sodium hydride (48.2 mg, 1.205 mmol) at 0° C. and stirred for 10 min. The reaction mixture was quenched and purification via C-18 flash column afforded the title compound (50 mg, 0.099 mmol, 24.62% yield) as a white.

LC-MS (ESI): m/z 481 [M+H]$^+$; 2.83min (ret time).

$^1$H NMR (400 MHz, DMSO-d$_6$): δ 8.70-8.68 (d, 1H), 7.67-7.66 (d, 1H), 7.47-7.45 (d, 2H), 7.33-7.31 (dd, 1H), 5.37 (s, 1H), 5.37-5.30 (q, 2H), 4.10-4.02 (m, 2H), 3.90-3.84 (m, 1H), 3.33-3.27 (m, 2H), 2.04-1.85 (m, 3H), 1.50-1.42 (m, 1H).

$^{19}$F NMR (376 MHz, DMSO-d$_6$): δ (ppm): −66.65, −126.83.

E2

(S)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

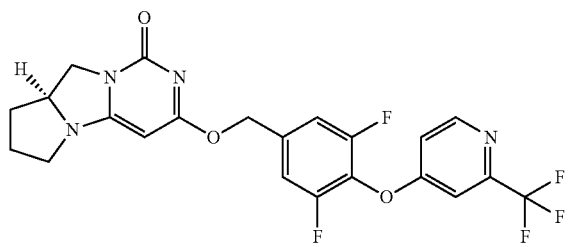 [SMILES: O=c1nc(OCc2cc(F)c(Oc3ccnc(C(F)(F)F)c3)c(F)c2)cc2n1C[C@@H]1CCCN21]

The title compound was prepared by a procedure similar to that described for 3-((3, 5-difluoro-4-((1-methyl-1H-pyrazol-4-yl)oxy)benzyl)oxy)-7,8, 8a, 9-tetrahydro pyrrolo [1', 2':3, 4] imidazo [1, 2-c] pyrimidin-1(6H)-one starting from (S)-3-chloro-7, 8, 8a, 9-tetrahydropyrrolo[1',2':3,4] imidazo[1,2-c]pyrimidin-1(6H)-one and (3,5-difluoro-4-((2-(trifluoromethyl)pyridin-4-yl)oxy)phenyl)methanol.

LC-MS (ESI): m/z 481 [M+H]$^+$; 3.04 min (ret time).

$^1$H NMR (400 MHz, DMSO-d$_6$): δ 8.70-8.68 (d, 1H), 7.68-7.67 (d, 1H), 7.47-7.45 (d, 2H), 7.33-7.31 (dd, 1H), 5.37 (s, 2H), 5.33 (s, 1H), 4.08-4.02 (m, 2H), 3.889-3.86 (m, 1H), 3.33-3.27 (m, 2H), 2.04-1.85 (m, 3H), 1.50-1.45 (m, 1H).

An exemplary process is provided: to a solution of (S)-3-chloro-7,8,8a,9-tetrahydropyrrolo[1',2':3,4]imidazo[1, 2-c]pyrimidin-1(6H)-one (57 mg, 0.269 mmol) and (3,5-difluoro-4-((2-(trifluoromethyl)pyridin-4-yl)oxy)phenyl) methanol (82 mg, 0.269 mmol) in DMF (10 mL) was added sodium hydride (32.3 mg, 0.808 mmol) at 0° C. and stirred for 10 min. The reaction mixture was quenched and purification via C-18 flash column afforded the title compound (45.8 mg, 0.091 mmol, 33.6° A, yield) as a white solid.

LC-MS (ESI): m/z 481 [M+H]$^+$; 3.04 min (ret time).

$^1$H NMR (400 MHz, DMSO-d$_6$): δ 8.70-8.68 (d, 1H), 7.68-7.67 (d, 1H), 7.47-7.45 (d, 2H), 7.33-7.31 (dd, 1H), 5.37 (s, 2H), 5.33 (s, 1H), 4.08-4.02 (m, 2H), 3.88-3.86 (m, 1H), 3.31-3.29 (m, 2H), 2.04-1.85 (m, 3H), 1.50-1.45 (m, 1H).

$^{19}$F NMR (376 MHz, DMSO-d$_6$): δ (ppm) : −66.62, −126.82.

C. Biological Assays and Data

The compounds of present invention are Lp-PLA$_2$ inhibitors, and may be useful in the treatment and prevention of diseases mediated by Lp-PLA$_2$. The biological activities of the compounds of present invention can be determined by using any suitable assay for determining the activity of a compound as a Lp-PLA$_2$ inhibitor, as well as tissue and in vivo models.

The biological activity data for each compound was either reported in at least one experiment or the average of multiple experiments. It is understood that the data described herein may have reasonable variations depending on the specific conditions and procedures used by the person conducting the experiments.

Lipoprotein-associated phospholipase A2 (Lp-PLA$_2$) biochemical assay (1) Recombinant human Lp-PLA$_2$ assays (rhLp-PLA$_2$)-PED6 assay N-((6-(2,4-dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labeled phospholipid, which is commercially available from Invitrogene and Molecular Probes. There is a quenching para-nitro phenyl (PNP) group in the sn3 position and a Bodipy fluorescein (FL) group in the sn2 position. Upon cleavage with Lp-PLA$_2$, the Bodipy FL group is liberated and then may result in an increase in fluorescence. Inhibitors of Lp-PLA$_2$ therefore prevent this cleavage and no fluorescent increase is observed.

The PED6 assay was run as an unquenched 10 µL assay. The source plate containing the compounds to be tested was prepared by making 1:3 (by volume) serial dilution of the compounds within DMSO on 384-well microplate. Then, 0.01 µL of the compounds on compound source plate were transferred into 384 well Greiner 784076 (black) plates using ECHO liquid dispenser. 5µL of recombinant human Lp-PLA$_2$ enzyme (4 nM (or 110 pM) rhLp-PLA$_2$ in assay buffer of 50 mM HEPES, pH 7.4, 150 mM NaCl, 1 mM CHAPS) was added to each well of the plate. Plates were centrifuged for 10 sec at 500 rpm. After 30 minutes preincubation, 5 μL of substrate (4 μM (or 5 μM) PED6 [from 5 mM DMSO stock] in assay buffer of 50 mM HEPES, pH 7.4, 150 mM NaCl, 1 mM CHAPS) was added to 384 well Greiner 784076 (black) plates. Plates were centrifuged for 10 sec at 500 rpm. The plate was covered to protect it from light and incubated for 20 min at room temperature. The plates were read for fluorescence intensity at ex: 480/em: 540 using ViewLux microplate imager for Envision spectrofluroimeters. pIC50 data, curve and QC analysis was conducted by using XL fit module in Excel.

Examples 1 and 2 were tested in the PED6 assay. The pIC$_{50}$ value for compounds tested was either reported in at least one experiment or the average of multiple experiments.

For example, the pIC50 values of recombinant human Lp-PLA$_2$ assay for following examples are:

| Example No. | rhLp-PLA$_2$ (pIC50) |
|---|---|
| 1 | 9.8 |
| 2 | 9.5 |

(2) PLA2 VIIB assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, PLA2 VIIB liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds between PLA2 VIIB and Lp-PLA$_2$.

The PLA2 VIIB assay was applied as an unquenched 10 μL assay. The source plate containing the compounds is prepared by making 1:3 (by volume) serial dilution of the compounds with pure DMSO on 384-well microplate. 0.01 μL of compounds on the compound source plate were transferred into 384 well Greiner 784076 (black) plates by ECHO liquid dispenser. 5 μL of Novel Serine Dependent Lipase (NSDL) enzyme (5 nM NSDL in assay buffer of 50 mM HEPES, pH 7.4, 150 mM NaCl, 1 mM CHAPS) was added to each well. Alternatively, in some instances, this step was carried out by adding 10 μL of recombinant human PLA2 VIIB (200 pM rhPLA$_2$VIIB in assay buffer of 50 mM HEPES, pH 7.4, 150 mM NaCl, 1 mM CHAPS) to each well. Plates were centrifuged for 10 sec at 500 rpm. After 30 minutes preincubation, 5 μL of substrate (5 μM PED6 [from 5 mM DMSO stock] in assay buffer of 50mM HEPES, pH 7.4, 150 mM NaCl, 1 mM CHAPS) was added to 384 well Greiner 784076 (black) low-volume plates. Plates were kinetic read by starting read immediately after PED6 addition at ex: 480/em: 540 using ViewLux microplate reader of Envision spectrofluorimeters. IC 50 data (which may be converted to pIC50 data), curve and QC analysis was conducted using XLfit module in Excel.

Examples 1 and 2 were tested in the PLA2 VIIB assay described above. Both examples had at least 100 fold selectivity between human recombinant Lp-PLA$_2$ and PLA2 VIIB.

(3) Lipoprotein-associated phospholipase A2 (Lp-PLA$_2$) Human Plasma assay-Thio-PAF assay The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluorescence after Michael addition of thiols. This assay may detect the activity of Lp-PLA$_2$ in human plasma, as determined by specific inhibition by Lp-PLA$_2$ inhibitors.

The thio-PAF assay was run as a quenched 15 μL assay. Compounds source plate was prepared by making 1:3 (by volume) serial dilution of the compounds into pure DMSO on 384-well microplate. 0.01 μpL of compounds on compound source plate were transferred to 384 well Greiner 784076 (black) low-volume plates by ECHO liquid dispenser. 8 μL pooled human plasma, which was previously aliquoted and frozen, was added. Plates were centrifuged for 10 sec at 500 rpm. After 30 minutes preincubation, 2 μL of substrate solution comprising 2.5mM 2-thio-PAF [from ethanol stock], 32 μM CPM [from a DMSO stock] and 3.2 mM NEM (N-ethylmaleimide) [made fresh daily in DMSO] in assay buffer of 50 mM HEPES, pH 7.4, 150 mM NaCl, 1 mM CHAPS was added to 384 well Greiner 784076 (black) low-volume plates by BRAVO liquid handling station. After 2 mins, reaction was quenched with 5 μL of 5% aqueous trifluoroacetic acid (TFA). Plates were covered to protect from light and incubated for 40 min at room temperature. Plates were read at ex: 380/em: 485 using Envision microplate reader. PIC50 data, curve and QC analysis were conducted by using XLFit module in Excel.

Examples 1 and 2 were tested in the Thio-PAF assay described above. The pIC$_{50}$ values for tested compounds were either reported in at least one experiment or the average of multiple experiments. The pIC$_{50}$ value in the Lp-PLA$_2$ human plasma assays for Example 1 was 8.1. The pIC50 value in the Lp-PLA$_2$ human plasma assays for Example 2 was 7.7.

D. Methods of Use

The compounds of the invention are inhibitors of Lp-PLA$_2$. Therefore, these compounds may be used in therapy, for example, in the treatment or prevention of diseases associated with the activity of Lp-PLA$_2$, which comprises treating a subject in need thereof with a therapeutically effective amount of an inhibitor of Lp-PLA$_2$. Accordingly, one aspect of the invention is directed to methods of treating or preventing diseases associated with the activity of Lp-PLA$_2$. As will be appreciated by those skilled in the art, a particular disease or its treatment may involve one or more underlying mechanisms associated with Lp-PLA$_2$ activity, including one or more of the mechanisms described herein.

In some embodiments, an inhibitor of Lp-PLA$_2$ according to the invention may be used in treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the compounds of the present invention may be used to treat or prevent any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the compounds of the present invention may be used to treat or prevent any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the compounds of the present invention may be used to lower the chances of having a cardiovascular event (such as a heart attack, myocardial infarction or stroke) in a patient with coronary heart disease.

In certain embodiments, the compounds of the present invention may be used to treat or prevent diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the compounds of the invention may be used for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides methods of treating or preventing a neurological disease associated with an abnormal blood brain barrier (BBB) function, inflammation, and/or microglia activation in a subject in need thereof. In some embodiments, the present invention provides methods of treating a neurological disease associated with an abnormal blood brain barrier (BBB) function, inflammation, and/or microglia activation in a subject in need thereof. The methods comprise administering to the subject a therapeutically effective amount of a compound of the present invention. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides methods of treating or preventing disease associated with a subject with blood brain barrier (BBB) leakage. In some embodiments, the present invention provides methods of treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the compounds of the present invention may be used to treat or prevent a neurodegeneration disease in a subject. The methods comprise administering to a subject in need thereof a compound of the invention, e.g., as a pharmaceutical composition comprising a compound of the invention. In one embodiment, the compounds of the present invention may be used to treat a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier. In one embodiment, the subject which is administered an agent that inhibits the activity of Lp-PLA$_2$ is a human.

In one embodiment, the present invention provides methods of treating or preventing a subject with or at risk of vascular dementia. The methods comprise administering to the subject a compound of the invention, e.g., as a pharmaceutical composition comprising a therapeutically effective amount of a compound of the present invention. In one embodiment, the present invention provides methods of treating a subject with or at risk of vascular dementia. In a certain embodiment, the vascular dementia is associated with Alzheimer's disease.

In certain embodiments, the present invention provides methods of decreasing beta amyloid, referred to as "Aβ" accumulation in the brain of a subject. The methods comprise administering to a subject in need thereof a pharmaceutical composition comprising a therapeutically effective amount of a compound of the present invention. In a further embodiment, the beta amyloid is Abeta-42.

In certain embodiments, when a subject is administered a therapeutically effective amount of a compound of the present invention, the methods may further comprise administering to the subject another therapeutic agent that may be useful in treating the neurodegenerative disease for which the subject is being treated, or that may be a co-morbidity. In one embodiment, the present invention provides methods of slowing or delaying the progression of cognitive and function decline in patients with mild Alzheimer's disease. In certain embodiment, the compounds of the present invention described herein may be used as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides methods of slowing or delaying the progression of cognitive or function decline in a patient with mild or moderate Alzheimer's disease and/ or cerebrovascular disease (CVD) comprise administering a therapeutically effective amount of a compound of the present invention to the patient who has been administered an agent used to provide symptomatic treatment to Alzheimer's disease (e.g., ARICEPT® or memantine) for 6 months or longer.

In certain embodiments, the present invention relates to methods of treating or preventing metabolic bone diseases by administering to the subject in need thereof a therapeutically effective amount of a compound of the present invention. In some embodiments, the present invention relates to methods of treating metabolic bone diseases by administering to the subject in need thereof a therapeutically effective amount of a compound of the present invention. Exemplary metabolic bone diseases include, diseases associated with loss of bone mass and density including, but are not limited to, osteoporosis and osteopenic related diseases. Exemplary osteoporosis and osteopenic related diseases include, but are not limited to, bone marrow abnormalities, dyslipidemia, Paget's diseases, type II diabetes, metabolic syndrome, insulin resistance, hyperparathyroidism and related diseases. In a further embodiment, the subject in need thereof is a human.

It is believed that methods of preventing osteoporosis and/or osteopenic diseases described herein may be affected by inhibiting the expression of Lp-$PLA_2$ and/or inhibiting the protein activity of Lp-$PLA_2$. Accordingly, some embodiments of the present invention provide methods for inhibiting Lp-$PLA_2$ by blocking enzyme activity. In a further embodiment, methods for inhibiting Lp-$PLA_2$ by reducing and/or down-regulating the expression of Lp-$PLA_2$ RNA are provided. In a further embodiment, preventing and/or reducing loss of bone mass and/or loss of bone density leads to preventing or reducing symptoms associated with metabolic bone diseases such as osteoporosis and/or osteopenic diseases.

In certain embodiments, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene), a selective estrogen modulator (SERM), estrogen therapy, hormone replacement therapy (ET/HRT) and teriparatide may be used.

One aspect of the present invention provides methods for treating and/or preventing ocular diseases by administering a therapeutically effective amount of a compound of the present invention. In some embodiments, the present invention provides methods for treating ocular diseases by administering a therapeutically effective amount of a compound of the present invention. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. Further, in one embodiment, the present invention relates to methods for treating ocular diseases by administering a compound of the present invention to inhibit Lp-$PLA_2$. Exemplary ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-$PLA_2$ inhibitor to treat eye diseases are provided in WO2012/080497, which is incorporated by reference herein.

Further, some embodiments of the present invention provide methods for treating or preventing diabetic macular edema in a subject. In some embodiments, the present invention provides methods for treating diabetic macular edema in a subject. The method comprises administering to a subject in need thereof a therapeutically effective amount of a compound of the present invention.

In certain embodiments, the present invention provides methods of treating or preventing a subject with or at risk of macular edema. In some embodiments, the present invention provides methods of treating a subject with or at risk of macular edema. The methods comprise administering to the subject a therapeutically effective amount of a compound of the present invention. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides methods of treating or preventing glaucoma or macular degeneration. In some embodiments, the present invention provides methods of treating glaucoma or macular degeneration. The methods comprise administering to the subject a therapeutically effective amount of a compound of the present invention.

In one embodiment, the present invention provides methods of treating or preventing a disease associated with the breakdown of the inner blood-retinal barrier in a subject in need thereof. In one embodiment, the present invention provides methods of treating a disease associated with the breakdown of the inner blood-retinal barrier in a subject in need thereof. The methods comprise administering to the subject a therapeutically effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating or preventing posterior uveitis or any of these systemic inflammatory diseases by administering a therapeutically effective amount of a compound of the present invention. In one embodiment, the present invention provides methods for treating posterior uveitis or any of these systemic inflammatory diseases by administering a therapeutically effective amount of a compound of the present invention.

It is believed that Lp-$PLA_2$ inhibitors may have beneficial effects on diseases associated with M1/M2 macrophage polarization. The belief is based on the following studies. A study was carried out by GSK to investigate the relationship between M1/M2 macrophage polarization and different diseases. 94 human markers described in Martinez FO et al., which distinguished M1 and M2 phenotypes was used against a GSK subscribed GeneLogic database. (See Martinez FO et al. (2006) J Immunol 177, 7303-7311.) The Connectivity Map methodology described in Lamb J et al. was used to identify the fraction of samples in each disease state having expression characteristics consistent with a M1-favoring or M2-favoring macrophage population. (See Lamb J et al. (2006) Science 313, 1929-1935) (PMID 17008526)). The study showed that liver cirrhosis, skin psoriasis, atopic dermatitis, pulmonary emphysema, chronic pancreatitis, chronic gastritis, and aortic aneurysm have M1/M2 imbalance.

A further study was carried out to study the impact of Lp-$PLA_2$ inhibitors on modulating M1/M2 imbalance. In this study, rats were induced to develop experimental autoimmune encephalomyelitis (EAE) by immunization with myelin basic protein (MBP) antigen and treated with a known Lp-PLA$_2$ inhibitor: 5-(9-Methoxy-4-oxo-6,7-dihydro-4H-pyrimido[6,1-a]isoquinolin-2-yl)oxy)-2-(3-(trifluoromethyl)phenoxy)benzonitrile (See PCT application no. PCT/CN2011/001597). In this preventive treatment model, the compound was administered at day 0 (day of immunization) and continued to administer until day 22. The study lasted for 25 days. Rats were subsequently monitored for symptoms of EAE. Rats were immunized with MBP to develop EAE and symptoms were monitored daily. Plasma Lp-PLA$_2$ activity, OxLDL, and LysoPC concentration were determined at different time points through the course of EAE. The results showed that plasma Lp-PLA$_2$ activity, OxLDL, and LysoPC concentrations increased as the clinical EAE disease progressed in the model, which indicates that they played a role in the pathology development. Lp-PLA$_2$ inhibitor treatment led to reduction in clinical disease associated with decreased Lp-PLA$_2$ activity and LysoPC levels in rat EAE plasma. Hence, inhibition of Lp-PLA$_2$ activity is beneficial in ameliorating disease in the rat EAE model.

Ex vivo analysis of proinflammatory (M1) and anti-inflammatory (M2) markers in control and compound treated EAE rats. Splenic macrophages were harvested at day 13 post MBP-immunization and assayed for expression of a variety of markers by realtime PCR. CNS infiltrating cells were harvested and macrophages were analyzed for expression of M1 and M2 markers by realtime PCR. Treatment with compound resulted in the decrease in M1 markers and increase in M2 markers, which potentially indicated the possibility of anti-inflammation and tissue repair.

Therefore, in certain embodiments, the present invention provides methods of treating or preventing disease associated with macrophage polarization, for example, M1/M2 macrophage polarization. In some embodiments, the present invention provides methods of treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS) and other autoimmune diseases that are associated with macrophage polarization.

Treatment and or prevention of a disease associated with Lp-PLA$_2$ activity may be achieved using a compound of this invention as a monotherapy, or in dual or multiple combination therapy. For example, the compounds of the present invention may be used to treat or prevent the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp(a)). Examples of the above include, but are not limited to, cholesterol synthesis inhibitors such as statins, anti-oxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312. In one embodiment, the compounds of the present invention may be used with one or more statins. The statins are a well-known class of cholesterol lowering agents and include atorvastatin, simvarstatin, pravastatin, cerivastatin, fluvastatin, lovastatin and rosuvastatin. In a certain embodiment, the compounds of the present invention may be used with an anti-diabetic agent or an insulin sensitizer. In one embodiment, a compound of the present invention may be used with PPAR gamma activators, for instance GI262570 (GlaxoSmith-Kline) and the glitazone class of compounds such as rosiglitazone, troglitazone and pioglitazone. Such agents may be administered in therapeutically effective amounts, e.g., as is known in the art, or lesser or greater amounts than known in the art provided that the amount administered is therapeutically effective.

Combination therapy includes administration of the therapeutic agents in separate dosage forms or together in a single dosage form. Combination therapy may involve simultaneous administration or separate administration of the therapeutic agents, which may be substantially simultaneous or substantially separate administration. Typically, combination therapy will involve administration of each agent such that therapeutically effective amounts of each agent are present in the subject's body in at least an overlapping period.

One aspect of the present invention provides the use of a compound of the present invention for the preparation of a medicament for carrying out a method described herein.

In some embodiments, the present invention provides the use of a compound of the present invention for the preparation of a medicament for treating or preventing diseases associated with the activity of Lp-PLA$_2$.

In some embodiments, it provides the use of a compound of the present invention for prepration of a medicament for treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the present invention provides the use of a compound of the present invention for the preparation of a medicament for treating or preventing any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the present invention provides the use of a compound of the present invention for the preparation of a medicament for treating or preventing any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the present invention provides the use of a compound of the present invention for the preparation of a medicament for lowering the chances of having a cardiovascular event (such as a heart attack, myocardial infarction or stroke) in a patient with coronary heart disease.

In certain embodiments, the present invention provides the use of a compound of the present invention for the preparation of a medicament for treating or preventing diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the present invention provides the use of a compound of the present invention for the preparation of a medicament for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides the use of a compound of the present invention for the preparation of a medicament for treating or preventing a neurological disease associated with an abnormal blood brain barrier (BBB) function, inflammation, and/or microglia activation in a subject in need thereof. In some embodiments, the present invention provides the use of a compound of the present invention for the preparation of a medicament for treating a neurological disease associated with an abnormal blood brain barrier (BBB) function, inflammation, and/ or microglia activation in a subject in need thereof. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides use of a compound of the present invention for the preparation of a medicament for treating or preventing disease associated with a subject with blood brain barrier (BBB) leakage. In some embodiments, the present invention provides the use of a compound of the present invention for the preparation of a medicament for treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the present invention provides the use of a compound of the present invention for the preparation of a medicament for treating or preventing a neurodegeneration disease in a subject. In one embodiment, the present invention provides the use of a compound of the present invention for the preparation of a medicament for treating a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier.

In one embodiment, the present invention provides the use of a compound of the present invention for the preparation of a medicament for treating or preventing a subject with or at risk of vascular dementia. In one embodiment, the present invention provides the use of a compound of the present invention for the preparation of a medicament for treating a subject with or at risk of vascular dementia. In a certain embodiment, the vascular dementia is associated with Alzheimer's disease.

In certain embodiments, the present invention provides the use of a compound of the present invention for the preparation of a medicament for decreasing beta amyloid, referred to as "Aβ" accumulation in the brain of a subject. In a further embodiment, the beta amyloid is Abeta-42.

In one embodiment, the present invention provides the use of a compound of the present invention for the preparation of a medicament for slowing or delaying the progression of cognitive function decline in patients with mild Alzheimer's disease. In certain embodiment, the present invention provides the use of a compound of the present invention for the preparation of a medicament as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides the use of a compound of the present invention for the preparation of a medicament for slowing or delaying the progression of cognitive function decline in a patient with mild or moderate Alzheimer's disease and/ or cerebrovascular disease (CVD), wherein the patient who has been administered an agent used to provide symptomatic treatment to Alzheimer's disease (e.g., ARICEPT® or memantine) for 6 months or longer. In certain embodiments, the present invention provides the use of a compound of the present invention for the preparation of a medicament for slowing or delaying the progression of cognitive function decline in a patient with mild or moderate Alzheimer's disease and cerebral small vessel disease (SVD), wherein the patient who has been administered an agent used to provide symptomatic treatment to Alzheimer's disease (e.g., ARICEPT® or memantine) for 6 months or longer.

In certain embodiments, the present invention provides the use of a compound of the present invention for the preparation of a medicament for treating or preventing metabolic bone diseases. In some embodiments, the present invention provides the use of a compound of the present invention for the preparation of a medicament for treating metabolic bone diseases. Exemplary metabolic bone diseases include, diseases associated with loss of bone mass and density including, but are not limited to, osteoporosis and osteopenic diseases. Exemplary osteoporosis and osteopenic diseases include, but are not limited to, bone marrow abnormalities, dyslipidemia, Paget's diseases, type II diabetes, metabolic syndrome, insulin resistance, hyperparathyroidism and related diseases. In a further embodiment, the present invention provides the use of a compound of the present invention for the preparation of a medicament for preventing and/or reducing loss of bone mass and/or loss of bone density leads to preventing or reducing symptoms associated with metabolic bone diseases such as osteoporosis and/or osteopenic diseases.

In certain embodiments, the present invention provides the use of a compound of the present invention for the preparation of a medicament for treating metabolic bone diseases, wherein the medicament is used with additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene), a selective estrogen modulator (SERM), estrogen therapy, hormone replacement therapy (ET/HRT) and teriparatide may be used.

One aspect of the present invention provides the use of a compound of the present invention for the preparation of a medicament for treating and/or preventing ocular diseases. In some embodiments, the present invention provides the use of a compound of the present invention for the preparation of a medicament for treating ocular diseases. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. More ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-PLA$_2$ inhibitor to treat eye diseases are provided in WO2012/080497, which is incorporated by reference herein.

Further, some embodiments of the present invention provide the use of a compound of the present invention for the preparation of a medicament for treating or preventing diabetic macular edema in a subject. In some embodiments, the present invention provides the use of a compound of the present invention for treating diabetic macular edema in a subject.

In certain embodiments, the present invention provides the use of a compound of the present invention for the preparation of a medicament for treating or preventing a subject with or at risk of macular edema. In some embodiments, the present invention provides the use of a compound of the present invention for the preparation of a medicament for treating a subject with or at risk of macular edema. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides the use of a compound of the present invention for the preparation of a medicament for treating or preventing glaucoma or macular degeneration. In some embodiments, the present invention provides the use of a compound of the present invention for the preparation of a medicament for treating glaucoma or macular degeneration.

In one embodiment, the present invention provides the use of a compound of the present invention for the preparation of a medicament for treating or preventing a disease associated with the breakdown of the inner blood-retinal barrier in a subject in need thereof. In one embodiment, the present invention provides the use of a compound of the present invention for the preparation of a medicament for treating a disease associated with the breakdown of the inner blood-retinal barrier in a subject in need thereof.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. In one embodiment, the present invention provides the use of a compound of the present invention for the preparation of a medicament for treating posterior uveitis or any of these systemic inflammatory diseases.

In certain embodiments, the present invention provides the use of a compound of the present invention for the preparation of a medicament for treating or preventing disease associated with macrophage polarization, for example, M1/M2 macrophage polarization. In some embodiments, the present invention provides the use of a compound of the present invention for the preparation of a medicament for treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS), ischemic cardiomyopathy, chronic heart failure post myocardial infarction (MI) and other autoimmune diseases that are associated with macrophage polarization.

Another aspect of the present invention provides a compound of the present invention for use in carrying out methods of treatment or prevention described herein. A further aspect of the present invention provides a compound described herein or a pharmaceutically acceptable salt thereof, for use in therapy.

In some embodiments, the present invention provides a compound of the present invention for use in treating or preventing diseases associated with the activity of Lp-PLA$_2$.

In some embodiments, the present invention provides a compound of the present invention for use in treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the present invention provides a compound of the present invention for use in treating or preventing any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the present invention provides a compound of the present invention for use in treating or preventing any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the present invention provides a compound of the present invention for use in lowering the chances of having a cardiovascular event (such as a heart attack, myocardial infarction or stroke) in a patient with coronary heart disease.

In certain embodiments, the present invention provides a compound of the present invention for use in treating or preventing diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the present invention provides a compound of the present invention for use in the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides a compound of the present invention for use in treating or preventing a neurological disease associated with an abnormal blood brain barrier (BBB) function, inflammation, and/or microglia activation in a subject in need thereof. In some embodiments, the present invention provides a compound of the present invention for use in treating a neurological disease associated with an abnormal blood brain barrier (BBB) function, inflammation, and/or microglia activation. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides a compound of the present invention for use in treating or preventing disease associated with a subject with blood brain barrier (BBB) leakage. In some embodiments, the present invention provides a compound of the present invention for use in treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the present invention provides a compound of the present invention for use in treating or preventing a neurodegeneration disease in a subject. In one embodiment, the present invention provides a compound of the present invention for use in treating a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier.

In one embodiment, the present invention provides a compound of the present invention for use in treating or preventing a subject with or at risk of vascular dementia. In one embodiment, the present invention provides a compound of the present invention for use in treating a subject with or at risk of vascular dementia. In a certain embodiment, the vascular dementia is associated with Alzheimer's disease.

In certain embodiments, the present invention provides a compound of the present invention for use in decreasing beta amyloid, referred to as "Aβ" accumulation in the brain of a subject. In a further embodiment, the beta amyloid is Abeta-42.

In one embodiment, the present invention provides a compound of the present invention for use in slowing or delaying the progression of cognitive function decline in patients with mild Alzheimer's disease. In certain embodiment, the present invention provides a compound of the present invention for use as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides a compound of the present invention for use in slowing or delaying the progression of cognitive function decline in a patient with mild or moderate Alzheimer's disease and/or cerebrovascular disease (CVD), wherein the patient who has been administered an agent used to provide symptomatic treatment to Alzheimer's disease (e.g., ARICEPT® or memantine) for 6 months or longer. In certain embodiments, the present invention provides a compound of the present invention for use in slowing or delaying the progression of cognitive function decline in a patient with mild or moderate Alzheimer's disease and cerebral small vessel disease (SVD), wherein the patient who has been administered an agent used to provide symptomatic treatment to Alzheimer's disease (e.g., ARICEPT® or memantine) for 6 months or longer.

In certain embodiments, the present invention provides a compound of the present invention for use in treating or preventing metabolic bone diseases. In some embodiments, the present invention provides a compound of the present invention for use in treating metabolic bone diseases. Exemplary metabolic bone diseases include, diseases associated with loss of bone mass and density including, but are not limited to, osteoporosis and osteopenic diseases. Exemplary osteoporosis and osteopenic diseases include, but are not limited to, bone marrow abnormalities, dyslipidemia, Paget's diseases, type II diabetes, metabolic syndrome, insulin resistance, hyperparathyroidism and related diseases. In a further embodiment, the present invention provides a compound of the present invention for use in preventing and/or reducing loss of bone mass and/or loss of bone density leads to preventing or reducing symptoms associated with metabolic bone diseases such as osteoporosis and/or osteopenic diseases.

In certain embodiments, the present invention provides a compound of the present invention for use in treating metabolic bone diseases, wherein the medicament is used with additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene), a selective estrogen modulator (SERM), estrogen therapy, hormone replacement therapy (ET/HRT) and teriparatide may be used.

One aspect of the present invention provides a compound of the present invention for use the use in treating and/or preventing ocular diseases. In some embodiments, the present invention provides a compound of the present invention for use in treating ocular diseases. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. More ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-PLA$_2$ inhibitor to treat eye diseases are provided in WO2012/080497, which is incorporated by reference herein.

Further, some embodiments of the present invention provide a compound of the present invention for use in treating or preventing diabetic macular edema in a subject. In some embodiments, the present invention provides a compound of the present invention for use in treating diabetic macular edema in a subject.

In certain embodiments, the present invention provides a compound of the present invention for use in treating or preventing a subject with or at risk of macular edema. In some embodiments, the present invention provides a compound of the present invention for use in treating a subject with or at risk of macular edema. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides a compound of the present invention for use in treating or preventing glaucoma or macular degeneration. In some embodiments, the present invention provides a compound of the present invention for use in treating glaucoma or macular degeneration.

In one embodiment, the present invention provides a compound of the present invention for use in treating or preventing a disease associated with the breakdown of the inner blood-retinal barrier in a subject in need thereof. In one embodiment, the present invention provides a compound of the present invention for use in treating a disease associated with the breakdown of the inner blood-retinal barrier in a subject in need thereof.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. In one embodiment, the present invention provides a compound of the present invention for use in treating posterior uveitis or any of these systemic inflammatory diseases.

In certain embodiments, the present invention provides a compound of the present invention for use in treating or preventing disease associated with macrophage polarization, for example, M1/M2 macrophage polarization. In some embodiments, the present invention provides the use of a compound of the present invention for the preparation of a medicament for treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS), ischemic cardiomyopathy, chronic heart failure post myocardial infarction (MI) and other autoimmune diseases that are associated with macrophage polarization.

E. Composition

The compounds of the present invention may be formulated into pharmaceutical compositions prior to administration to a subject. Accordingly, one aspect of the invention is directed to pharmaceutical compositions comprising a compound of the invention and a pharmaceutically acceptable excipient. In accordance with another aspect of the invention, a process is provided for the preparation of a pharmaceutical composition including admixing a compound described above or salts thereof, solvates etc thereof, with one or more pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1g of a compound of the present invention, depending on the condition being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of present invention for the treatment of the disease described herein will generally be in the range of 0.1 to 100 mg/kg body weight of recipient per day and more usually in the range of 1 to 10 mg/kg body weight per day. Thus, for example, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. It is envisaged that similar dosages would be appropriate for treatment of the other conditions referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound described above with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically acceptable excipients may vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds described above described herein or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

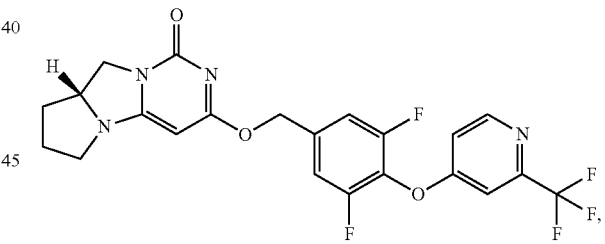

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg of a compound having the structure of

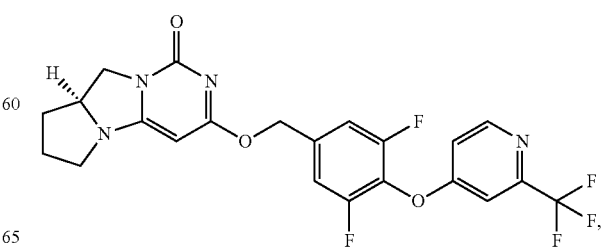

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

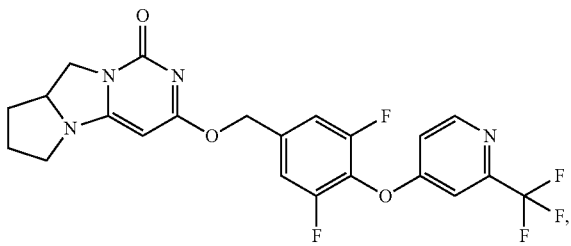 [SMILES: O=c1nc(OCc2cc(F)c(Oc3ccnc(C(F)(F)F)c3)c(F)c2)cc2n1CC1CCCN21]

or a pharmaceutically acceptable salt thereof and 0.01 to 5 g of one or more pharmaceutically acceptable excipients.

In another embodiment, the present invention is directed a pharmaceutical composition for the treatment of neurodegeneration disease comprising a compound described herein or a pharmaceutically acceptable salt thereof and a pharmaceitucally acceptable excipient. In another embodiment, the present invention is directed a pharmaceutical composition for the treatment of Alzheimer's disease comprising a compound described herein or a pharmaceutically acceptable salt thereof and a pharmaceutically acceptable excipient.

What is claimed is:

1. A compound which is

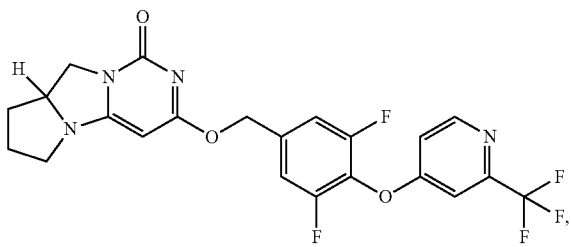

or a salt thereof.

2. A compound which is

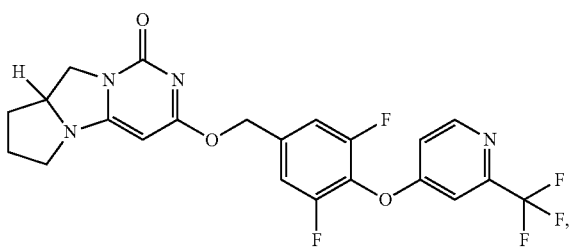 [SMILES: O=c1nc(OCc2cc(F)c(Oc3ccnc(C(F)(F)F)c3)c(F)c2)cc2n1CC1CCCN21]

or a pharmaceutically acceptable salt thereof.

3. The compound according to claim 1 which is (R)-3-((3, 5-difluoro-4-((2-(trifluoromethyl) pyridin-4-yl) oxy) benzyl) oxy)-7, 8, 8a, 9-tetra hydropyrrolo[1',2':3 ,4]imidazo [1,2-c]pyrimidin-1(6H)-one

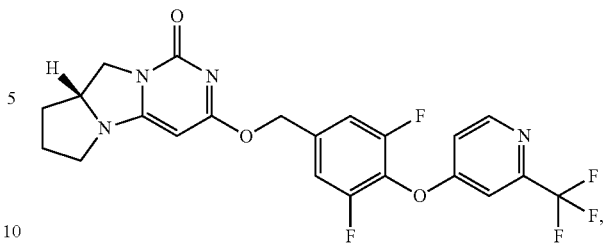

or a pharmaceutically acceptable salt thereof.

4. The compound according to claim 1 which is (R)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

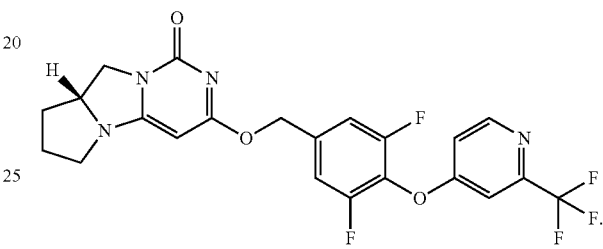

5. The compound according to claim 1 which is a pharmaceutically acceptable salt of (R)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pynmidin-1(6H)-one

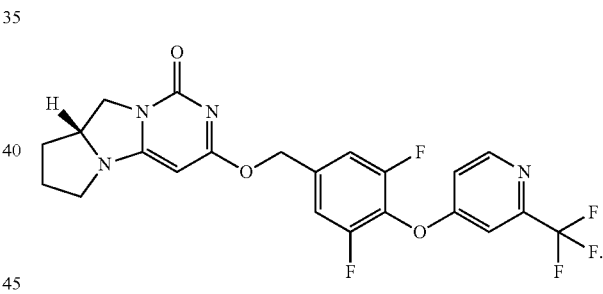

6. The compound according to claim 1 which is (S)-3-((3, 5-difluoro-4-((2-(trifluoromethyl) pyridin-4-yl) oxy) benzyl) oxy)-7, 8, 8a, 9-tetra hydropyrrolo[1',2':3 ,4]imidazo[1,2-c]pyrimidin-1(6H)-one

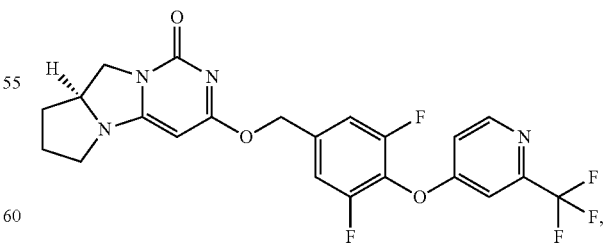

or a pharmaceutically acceptable salt thereof.

7. The compound according to claim 1, which is (S)-3-((3, 5-difluoro-4-((2-(trifluoromethyl) pyridm-4-yl) oxy) benzyl) oxy)-7, 8, 8a, 9-tetra hydropyrrolo[1',2':3 ,4]imidazo[1,2-c]pyrimidin-1(6H)-one

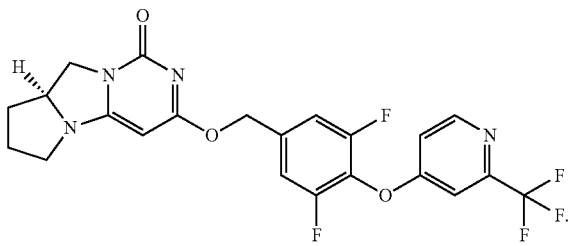

8. The compound according to claim 1, which is a pharmaceutically acceptable salt of (S)-3-((3, 5-difluoro-4-((2-(trifluoromethyl) pyridm-4-yl) oxy) benzyl) oxy)-7, 8, 8a, 9-tetra hydropyrrolo[1',2':3,4]imidazo[1,2-c]pyrimidin-1(6H)-one

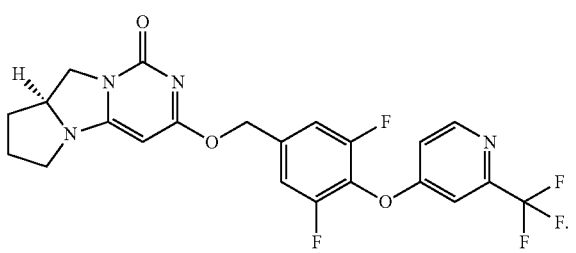

9. A pharmaceutical composition comprising a compound having a structure of

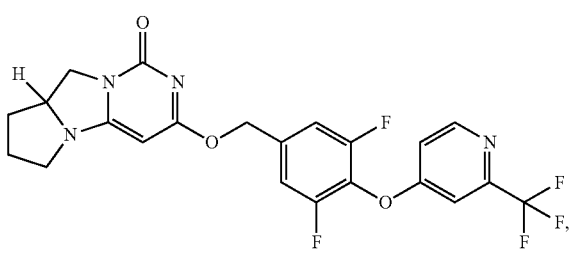

or a pharmaceutically acceptable salt thereof, and a pharmaceutically acceptable excipient.

10. The pharmaceutical composition according to claim 9 wherein the compound has the structure of

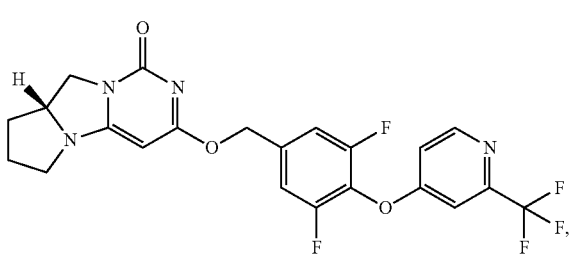 [SMILES: O=c1nc(OCc2cc(F)c(Oc3ccnc(C(F)(F)F)c3)c(F)c2)cc2n1C[C@H]1CCCN21]

or a pharmaceutically acceptable salt thereof.

11. The pharmaceutical composition according to claim 9 wherein the compound has the structure of

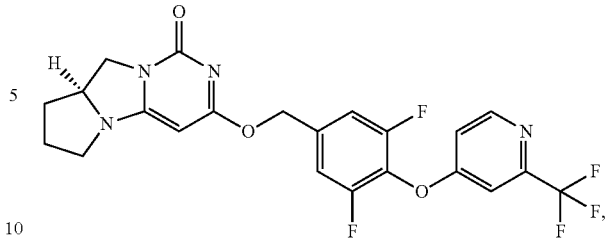

or a pharmaceutically acceptable salt thereof.

12. A method for treating neurodegeneration disease in a subject in need thereof comprising administering to the subject a therapeutically effective amount of a compound having a structure of

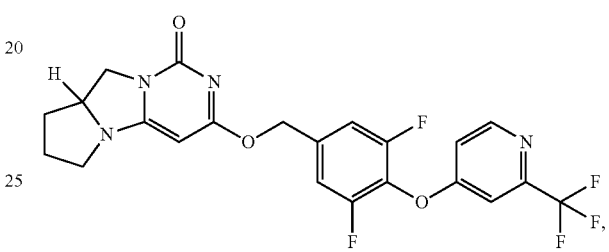

or a pharmaceutically acceptable salt thereof.

13. The method according to claim 12, wherein the neurodegeneration disease is Alzheimer's disease.

14. The method according to claim 12, wherein the compound has the structure of

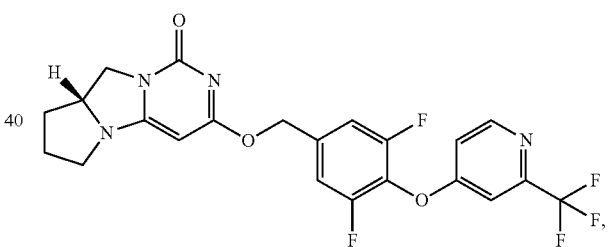

or a pharmaceutically acceptable salt thereof.

15. The method according to claim 12, wherein the compound has the structure of

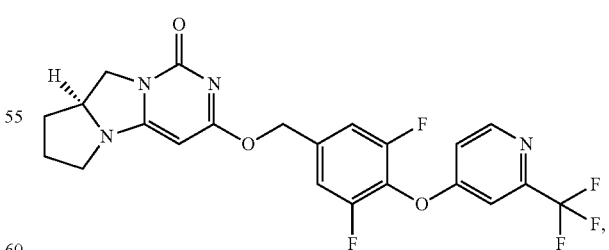

or a pharmaceutically acceptable salt thereof.

16. The method according to claim 12, wherein the subject is human.

* * * * *